US010844317B2

(12) United States Patent
Okuyama et al.

(10) Patent No.: US 10,844,317 B2
(45) Date of Patent: Nov. 24, 2020

(54) LIPID COMPOSITION AND METHOD FOR PRODUCING SAME

(71) Applicant: IHI CORPORATION, Tokyo (JP)

(72) Inventors: Junichi Okuyama, Tokyo (JP); Tomomi Yajima, Tokyo (JP); Koretaro Takahashi, Sapporo (JP); Takeya Yoshioka, Hakodate (JP)

(73) Assignee: IHI CORPORATION, Tokyo (JP)

( * ) Notice: Subject to any disclaimer, the term of this patent is extended or adjusted under 35 U.S.C. 154(b) by 0 days.

(21) Appl. No.: 16/273,499

(22) Filed: Feb. 12, 2019

(65) Prior Publication Data
US 2019/0169530 A1   Jun. 6, 2019

Related U.S. Application Data

(60) Division of application No. 15/702,856, filed on Sep. 13, 2017, now Pat. No. 10,246,663, which is a (Continued)

(30) Foreign Application Priority Data

Mar. 18, 2015 (JP) ................................ 2015-054348

(51) Int. Cl.
*C11B 1/10* (2006.01)
*B01D 11/02* (2006.01)
(Continued)

(52) U.S. Cl.
CPC . *C11B 1/10* (2013.01); *A23J 7/00* (2013.01); *B01D 11/02* (2013.01); *C11B 3/006* (2013.01); (Continued)

(58) Field of Classification Search
CPC ... C11C 3/10; C11B 1/10; C11B 3/006; C11B 3/10; B01D 11/02; B01D 11/0215
See application file for complete search history.

(56) References Cited

U.S. PATENT DOCUMENTS 8,148,120 B2 *   4/2012  Beecher .................... C10L 1/02
                                                                    435/134
8,202,425 B2 *   6/2012  Kale .......................... C11B 1/10
                                                                    203/39
(Continued)

FOREIGN PATENT DOCUMENTS

CN          1649988 A      8/2005
CN        103582694 A      2/2014
(Continued)

OTHER PUBLICATIONS

Folch, J. et al., A simple method for the isolation and purification of total lipids from animal tissues, 1957, Journal of Biological Chemistry, vol. 226, pp. 497-509 (Year: 1957).*
(Continued)

*Primary Examiner* — Yate' K Cutliff

(57) ABSTRACT

The method of producing a lipid composition comprises an extraction treatment step to extract a lipid comprised in a hydrated raw material by using an extraction solvent comprising a polar solvent and a nonpolar solvent, and a separation treatment step to separate an extract solution obtained in the extraction treatment step into a polar solvent phase comprising a first lipid fraction and a nonpolar solvent phase comprising a second lipid fraction.

20 Claims, 5 Drawing Sheets

Related U.S. Application Data continuation of application No. PCT/JP2016/058735, filed on Mar. 18, 2016.

(51) Int. Cl.

| | | |
|---|---|---|
| *A23J 7/00* | (2006.01) | |
| *C11B 11/00* | (2006.01) | |
| *C11B 3/00* | (2006.01) | |
| *C11B 3/10* | (2006.01) | |
| *C11C 3/00* | (2006.01) | |
| *C12P 7/64* | (2006.01) | |

(52) U.S. Cl.
CPC ............... *C11B 3/10* (2013.01); *C11B 11/00* (2013.01); *C11C 3/00* (2013.01); *C12P 7/64* (2013.01)

(56) References Cited

U.S. PATENT DOCUMENTS

| | | | | |
|---|---|---|---|---|
| 8,383,845 B2 * | 2/2013 | Catchpole et al. | ....... | C11B 1/00 554/20 |
| 2003/0190392 A1 | 10/2003 | Hiratsuka et al. | | |
| 2010/0160659 A1 | 6/2010 | Catchpole et al. | | |
| 2011/0189374 A1 | 8/2011 | Yoshikawa | | |
| 2011/0189760 A1 | 8/2011 | Yoshikawa | | |
| 2012/0053357 A1 | 3/2012 | Kale | | |
| 2013/0274490 A1 * | 10/2013 | Hippler | ..................... | C11B 1/10 554/19 |

FOREIGN PATENT DOCUMENTS

| | | | | |
|---|---|---|---|---|
| JP | S60-055096 A | | 3/1985 | |
| JP | H02-008298 A | | 1/1990 | |
| JP | H08-325192 A | | 12/1996 | |
| JP | H11-075884 A | | 3/1999 | |
| JP | H11-116983 A | | 4/1999 | |
| JP | 2000-060432 A | * | 2/2000 | ................ A23J 7/00 |
| JP | 2000-060432 A | | 2/2000 | |
| JP | 2005-112819 A | | 4/2005 | |
| JP | 2005-179340 A | | 7/2005 | |
| JP | 2008-255182 A | | 10/2008 | |
| JP | 2009-538366 A | | 11/2009 | |
| JP | 2010-095556 A | | 4/2010 | |
| JP | 2010-159383 A | | 7/2010 | |
| WO | 2010/035749 A1 | | 4/2010 | |
| WO | 2012/138382 A1 | | 10/2012 | |

OTHER PUBLICATIONS

Saito, Hiroaki, et al., Characteristics of the lipid and fatty acid compositions of the Humbold squid, Dosidicus gigas: The trophic relationship between squid and its prey, 2014, Eur. J. Lipid Sci. Technology, vol. 116, issue 3, pp. 360-366 (Year: 2014).*

Hiroaki Sato et al., "Characteristics of the lipid and fatty acid compositions of the Humboldt squid, Dosidicus gigas: The trophic relationship between the squid and its prey", European Journal of Lipid Science and Technology, 2014, vol. 116, No. 3, pp. 360-366.

Joseph C. Gigliotti et al., "Extraction and characterisation of lipids from Antarctic krill (*Euphausia superba*)", Food Chemistry, 2011, vol. 125, No. 3, pp. 1028-1036.

International Search Report received for PCT Patent Application No. PCT/JP2016/058735 dated Jun. 21, 2016, 4 page (2 pages of English translation of International Search Report, 2 pages of International Search Report).

European Patent Office, "Extended European Search Report," issued in European Patent Application No. 16 765 111.6, which is a European counterpart of U.S. Appl. No. 15/702,856, with an issuance date of Feb. 9, 2018, 7 pages.

Hisashi Matsubara et al., "Development of an extraction procedure of crude ceramide from unused portion of Humboldt squid (*Dosidicus gigas*) II", Report of Aomori Prefectural Industrial Technology Research Center Food Research Institute, 2012, vol. 3, pp. 25-29.

Japan Patent Office, "Office Action," issued in Japanese Patent Application No. JP 2017-506220, which is a Japanese counterpart of U.S. Appl. No. 15/702,856, dated Jan. 29, 2019, 3 pages.

The China National Intellectual Property Administration, "First Office Action," issued in Chinese Patent Application No. 201680015647. 9, which is a counterpart to U.S. Appl. No. 16/273,499, dated Mar. 4, 2020, 14 pages (1 page of partial English translation of Office Action, and 13 pages of original Chinese Office Action).

Yu Lanlan et al., "Modem Biochemical Separation Technology and Application Research", pp. 121-127, ISBN 978-7-5601-7939-1, Dec. 2011, Jilin University Press.

* cited by examiner

LIPID COMPOSITION AND METHOD FOR PRODUCING SAME

CROSS REFERENCE TO RELATED APPLICATIONS

This application is a divisional application of co-pending U.S. application Ser. No. 15/702,856, filed on Sep. 13, 2017, which is a continuation application of International Application No. PCT/JP2016/058735, filed on Mar. 18, 2016, which claims priority to Japanese Patent Application No. 2015-054348, filed on Mar. 18, 2015, the entire contents of which are incorporated herein by reference.

BACKGROUND

Technical Field

The present disclosure relates to a lipid composition and a method for producing the same. More specifically, the present disclosure relates to a lipid composition comprising a triacylglycerol and a phospholipid, rich in unsaturated fatty acids such as eicosapentaenoic acid (EPA) and docosahexaenoic acid (DHA), and to a method for producing the lipid composition from an aquatic product resource or from a byproduct or the like that is generated during the processing of the aquatic product resource.

Description of the Related Art

The highly unsaturated fatty acids include Ω6 fatty acids such as γ-linolenic acid and arachidonic acid and ω3 fatty acids such as α-linolenic acid, EPA, and DHA, and they are known as the essential fatty acids that are not readily synthesized within the body. The ω3 fatty acids such as EPA and DHA, especially, are actively utilized in foods, functional foods, pharmaceuticals, and the like, as useful substances having a variety of physiological functions such as reduction of blood neutral fat and alleviation of rheumatoid arthritis symptoms. The physiological functions of EPA and DHA are similar but not identical to each other, and there is a benefit in taking each of the ω3 fatty acids. For EPA, in particular, there have been reports of excellent health-related functionalities not seen in DHA and the physiological activities involving eicosanoid production including the suppressive effect on the platelet aggregation and the anti-inflammatory effect.

Conventionally, ω3 unsaturated fatty acids have been obtained as fish oil by boil-extracting the oils and the fats from blue fish, e.g. pilchards. Fish oil has a low phospholipid content and it comprises ω3 fatty acids mainly in the form of triacylglycerols. On the other hand, the midgut glands, gonads, mantles, and gills of Hotate-gai (Yesso scallops), as well as the eyeballs, buccal bulbs, and skins of squids, comprise phospholipids in addition to triacylglycerols. Further, the triacylglycerols and the phospholipids comprise unsaturated fatty acids via ester bonds, EPA and DHA being typical examples. In the Western countries, krill oil (derived from Antarctic krill) is commercially distributed as a lipid product containing EPA and DHA in the phospholipid-bound form.

The patent literatures 1 to 6 listed below disclose the methods for producing the lipids comprising EPA or DHA in the phospholipid-bound form from the byproducts generated during the processing of Hotate-gai or Surume-ika (Japanese flying squids).

Patent Literature 1: Japanese Patent Application Laid-Open Publication No. 2000-60432
Patent Literature 2: Japanese Patent Application Laid-Open Publication No. 2008-255182
Patent Literature 3: Japanese Patent Application Laid-Open Publication No. 2010-159383
Patent Literature 4: Japanese Patent Application Laid-Open Publication No. H08-325192
Patent Literature 5: Japanese Patent Application Laid-Open Publication No. H02-8298
Patent Literature 6: Japanese Patent Application Laid-Open Publication No. H11-116983

SUMMARY

Regarding the bioabsorbability of the unsaturated fatty acids, the comparative studies of the triacylglycerols and the phospholipids have shown that the phospholipid-bound ω3 fatty acids have better bioabsorbability than the triacylglycerol-bound ω3 fatty acids. Thus, increasing demands for the lipid compositions comprising the phospholipid-bound ω3 fatty acids will be expected. However, since the conventional methods of manufacture described in the above-mentioned Patent Literatures 1 to 5 extract the lipids from the dry materials, they require a large amount of energy for drying the raw materials. Regardless of whether the raw materials richly contain phospholipids or not, when the lipids are to be extracted from the dry materials, the need for such large energy input generally becomes problematic.

Moreover, Patent Literature 6 mentioned above separates and collects the oily fraction from the aqueous phase which has been treated with a protein-degrading enzyme. However, since the phospholipids have the hydrophilic moieties, emulsification could easily occur. As a result, separation and collection of the lipid fraction and the aqueous fraction become difficult. Therefore, this conventional method of manufacturing a lipid composition requires a centrifugation exceeding the usual 3000×g.

In order to obtain the lipids richly comprising EPA and DHA, the midgut glands, gonads, mantles, or gills of Hotate-gai, especially for the lipids comprising a high fraction of EPA, or the eyeballs, buccal bulbs, or skins of Surume-ika, especially for the lipids comprising a high fraction of DHA, may be preferably used as a raw material. However, the lipids of these raw materials richly comprise phospholipids. Therefore, they suffer from the above-mentioned problems stemming from the presence of the phospholipids. Therefore, there is a need to develop a practical technique by which a lipid composition comprising a high amount of EPA or DHA can be efficiently and inexpensively manufactured.

Moreover, by virtue of the food chain, heavy metals such as cadmium, arsenic (or arsenic-containing compounds), dioxins (polychlorinated dibenzo-para-dioxins, polychlorinated dibenzofurans, and dioxin-like polychlorinated biphenyls) and other compounds are accumulated in the aquatic product resources as well as the byproducts produced during the processing thereof. It may be preferable to remove these substances when the lipids extracted from the aquatic product resources or the processing byproducts thereof are used in a nutritional composition. In the conventional techniques, these substances will contaminate the lipids when the lipids are extracted from the raw materials. Thus, it was not easy to separate and remove the unwanted substances from the lipids intended for a nutritional composition. Thus, what is desired is a lipid composition wherein the inclusion of the heavy metals such as cadmium and the substances such as arsenic, dioxins, and the like is reduced, especially a lipid composition richly comprising phospholipids, EPA, and/or DHA wherein the inclusion of the heavy metals such as cadmium and the substances such as arsenic, dioxins, and the like is reduced, and a method that enables manufacture of such a lipid composition.

In one aspect, an object of the present disclosure is to provide a method of producing a lipid composition that solves the above-mentioned problems wherein extraction and isolation/purification of the lipids from a raw material can be performed in a simple and easy manner without the need of introducing a large amount of energy for drying the raw material.

In another aspect, an object of the present disclosure is to provide lipids that comprise phospholipids and richly comprise EPA and/or DHA as fatty acid components making up the lipids, wherein the inclusion of unwanted substances such as cadmium, arsenic, and dioxins is diminished.

The present inventors had conducted extensive research to solve the above problems, and as a result, found a method for efficiently obtaining the lipids by solvent extraction wherein the raw material is kept in a hydrated (wet) state and not dried.

According to one embodiment of the present disclosure, a method of producing a lipid composition is provided, the method comprising: an extraction treatment step to extract a lipid comprised in a hydrated raw material by using an extraction solvent comprising a mixture of a polar solvent and a nonpolar solvent; and a separation treatment step to separate an extract obtained in the extraction treatment step into a polar solvent phase comprising a first lipid fraction, a nonpolar solvent phase comprising a second lipid fraction, and a solid fraction phase (insoluble solid fraction phase).

The method of producing a lipid composition according to the embodiment of the present disclosure may further comprise a purification treatment step to remove an impurity from the nonpolar solvent phase by contacting the nonpolar solvent phase obtained in the separation treatment step with an adsorbent.

The method of producing a lipid composition according to the embodiment of the present disclosure may further comprise a solvent recovery step to recover the polar solvent and the nonpolar solvent from the polar solvent phase and the nonpolar solvent phase obtained in the separation treatment step, respectively.

The polar solvent may comprise a lower alcohol, acetone, acetonitrile, THF, DMF, or a combination thereof.

The nonpolar solvent may comprise an alkane with a carbon number of 5 to 8, diethyl ether, t-butyl methyl ether, ethyl acetate, chloroform, methylene chloride, benzene, toluene, or a combination thereof.

Three % by mass or more of the total lipid comprised in the hydrated raw material may be phospholipids.

For the extraction treatment step, the extraction solvent may be prepared beforehand as a mixed organic solvent with the polar solvent and the nonpolar solvent and then added to the hydrated raw material, or, the polar solvent and the nonpolar solvent may be added individually and sequentially to the hydrated raw material to prepare a mixed organic solvent by virtue of such additions.

The hydrated raw material may comprise at least one of byproducts generated during the processing of a Hotate-gai or a squid.

The hydrated raw material may comprise water at a water content of 60 to 85% by mass.

In the extraction treatment step, the polar solvent and the nonpolar solvent may be used at 2 to 4 parts by weight and 1 to 5 parts by weight, respectively, relative to 1 part by wet weight of the raw material.

The method of producing a lipid composition according to the embodiment of the present disclosure may further comprise a heat treatment step to heat the hydrated raw material at a temperature of 65° C. or higher.

The method of producing a lipid composition according to the embodiment of the present disclosure may further comprise a step of crushing (breaking up) the hydrated raw material. Some aspects of the method of producing a lipid composition according to the embodiment of the present disclosure are summarized in FIG. 1.

According to another embodiment of the present disclosure, an apparatus for producing a lipid composition is provided, the apparatus comprising:

an extraction treatment component for extracting a lipid comprised in a hydrated raw material by using a mixed extraction solvent comprising a polar solvent and a nonpolar solvent; and a separation treatment component for separating an extract obtained in the extraction treatment component into a polar solvent phase comprising a first lipid fraction, a nonpolar solvent phase comprising a second lipid fraction, and a solid fraction phase (insoluble solid fraction phase).

The apparatus for producing a lipid composition according to the embodiment of the present disclosure may further comprise a purification treatment component for contacting the nonpolar solvent phase separated in the separation treatment component with an adsorbent to remove an impurity from the nonpolar solvent phase.

The apparatus for producing a lipid composition according to the embodiment of the present disclosure may further comprise a solvent recovery component for recovering the polar solvent and the nonpolar solvent from the polar solvent phase and the nonpolar solvent phase separated in the separation treatment component, respectively.

According to another embodiment of the present disclosure, a lipid composition is provided, wherein the EPA to DHA mass ratio (EPA/DHA) in the fatty acids constituting the lipid is 1.2 to 7.2, the proportion of phospholipid in the total lipid is no lower than 3% by mass and no higher than 54% by mass, the cadmium concentration is 0.4 mg or lower per kg of lipid, the arsenic concentration is 3 mg or lower per kg of lipid, and the concentration of dioxins is 2 pg-TEQ or lower per gram of lipid. In the lipid composition according to this embodiment, the EPA to DHA mass ratio (EPADHA) in the fatty acids constituting the lipid may be 3.4 to 7.2 and the proportion of phospholipid in the total lipid may be no lower than 18% by mass and no higher than 39% by mass.

According to the present disclosure, a lipid composition can be manufactured at low cost overall because not only can the lipids be extracted from a hydrated raw material that is kept in a hydrated state and not dried, but the amount of addition (i.e. amount of use) of the polar solvent, which has a low recovery rate due to the co-boiling with water, can also be reduced. Moreover, according to the present disclosure, the lipid extraction can be performed with ease because emulsification does not occur regardless of whether the raw material richly contains phospholipids or not. Thus, a lipid composition comprising EPA and/or DHA can be manufactured efficiently also from those raw materials which richly contain EPA and/or DHA in addition to phospholipids.

Further, according to the present disclosure, the lipids can be separately obtained as a phospholipid-rich fraction and a neutral fat-rich fraction, via two-phase separation of the lipid-extracting liquid which uses a mixed organic solvent. Because of this, it is for example possible to prepare a lipid composition in a desired constitution by blending both fractions at an appropriate ratio, which makes it possible to provide a compositionally consistent lipid composition that is not affected by the variations in the constitutions of the raw materials caused by seasonal differences or regional differences. Further, this makes it possible to process the phospholipids and the neutral fats substantially separately, and therefore, a suitable enzymatic treatment etc. can be performed on each.

Further, according to the present disclosure, even if the byproducts generated during the processing of the aquatic resources are used as a raw material, the lipids comprised in these byproducts can be obtained free from the heavy metals such as cadmium, arsenic, and the substances such as dioxins, and therefore, the lipids that are safe and satisfy the food-related regulatory limits, wherein the concentrations of these impurities are extremely low, can be obtained through a fairly simple purification step. Therefore, the present disclosure will facilitate the utilization of the byproducts generated during the processing of the aquatic product resources such as Hotate-gai and Surume-ika, and will be useful for solving the problems relating to the disposal costs of the byproducts and for effective utilization of the marine resources.

DESCRIPTION OF THE EMBODIMENTS

Figure 1:
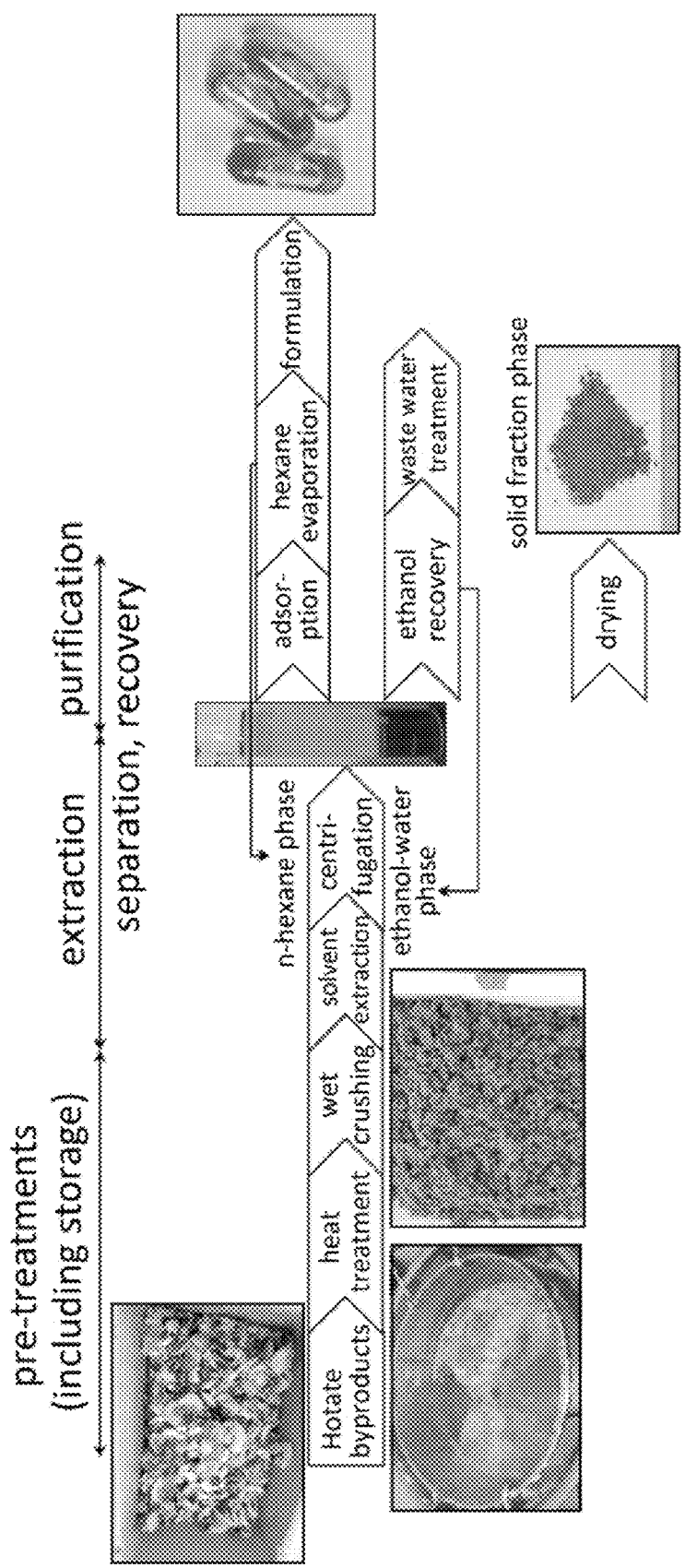
FIG. 1 shows an overview of the production of a lipid composition according to one embodiment of the present disclosure. In this embodiment, the lipid composition is obtained from the nonpolar solvent phase.

The lipids include simple lipids such as triacylglycerols and compound lipids such as phospholipids and glycolipids. These lipids comprise fatty acids as the components of the molecules, i.e. they comprise the fatty acids ester-bonded within the molecules, and will release the fatty acids upon hydrolysis. The fatty acids can be divided into saturated fatty acids and unsaturated fatty acids. Lauric acid, myristic acid, and the like are saturated fatty acids. On the other hand, ω3 fatty acids such as EPA and DHA and ω6 fatty acids such as arachidonic acid, which are the essential fatty acids that are not readily synthesized within the human body, are highly unsaturated fatty acids (or polyunsaturated fatty acids) having multiple unsaturated bonds.

The marine organisms such as pilchards and krill are known to be aquatic resources comprising ω3 fatty acids. By using these marine products as raw materials, a composition comprising the lipids such as triacylglycerols and phospholipids can be obtained. The ω3 fatty acids will be included in the composition as the constituents of the lipids. The resulting lipid compositions are used in such products as dietary supplements, food additives, and pharmaceuticals. With respect to bioabsorption of the fatty acids that constitute the lipid molecules, the phospholipid forms having the hydrophilic groups are more efficiently absorbed than the triacylglycerol forms. Therefore, a lipid composition richly comprising ω3 fatty acids in the form of phospholipids is especially useful as a supply source of the ω3 fatty acids.

The phospholipids have been extracted from dried raw materials. This is due to the fact that the phospholipids have a hydrophilic moiety (phosphate group). That is, in the solvent extraction in the co-presence of water, the phospholipids would act as surfactants, making it difficult to separate the lipids from the water. Regarding this point, the present disclosure performs extraction of the lipids by using organic solvents while the raw materials remain hydrated and not pre-dried. For this step, a mixed organic solvent is prepared by combining both polar and nonpolar solvents in a suitable ratio and used as an extraction solvent. It is thereby possible to extract favorably the amphiphilic phospholipids together with other lipid fractions such as triacylglycerols. The extraction treatment according to the present disclosure may be applied to the hydrated raw materials that are poor in phospholipids as well.

The lipids collected from the extracts comprise other lipids in addition to the phospholipids; specifically, neutral fats, most typically triacylglycerols, and lipophilic derived lipids (the compounds generated by hydrolysis of the lipids) such as sterols. In the present disclosure, the extract (the mixed organic solvent comprising the lipids) obtained by the extraction treatment is subjected to a separation treatment, to be separated into a polar solvent phase, a nonpolar solvent phase, and a solid fraction phase. The extract is thereby fractionated into the three phases, and the lipids, in particular, are separated into a first lipid fraction comprised in the polar solvent phase and a second lipid fraction comprised in the nonpolar solvent phase. The first lipid fraction in the polar solvent phase represents phospholipids and comprises little neutral fats. The second lipid fraction in the nonpolar solvent phase mainly comprises neutral fats but also comprises some amount of phospholipids.

It is noted that the extract also comprises, in addition to the phospholipids and the neutral fats, the impurities including heavy metals such as cadmium, lead, mercury, chromium, copper, and zinc, magnesium (or magnesium-containing compounds), arsenic (or arsenic-containing compounds), dioxins and the like, and organic compounds such as proteinous compounds. These heavy metals and magnesium, arsenic, dioxins and the like, and proteinous organic compounds are selectively separated into the polar solvent phase and the solid fraction phase. Therefore, these impurities can be separated from the lipids, as described below. In particular, when the extraction and the phase separation are carried out by using a mixed organic solvent according to the present disclosure, the heavy metals such as cadmium, lead, and mercury and the impurities such as magnesium, arsenic, dioxins, and the like will be separated into the polar solvent phase and the insoluble solid fraction phase and excluded from the nonpolar solvent phase in which the lipids are dissolved. Thus, an extremely low impurity content level can be easily attained in the nonpolar solvent phase.

Below, the method of producing a lipid composition of the present disclosure is described in detail.

In the present disclosure, the raw material for producing the lipid composition is a hydrated raw material comprising a lipid. In particular, the raw material is preferably a hydrated raw material comprising a phospholipid. The components making up the acyl ester moieties of the lipid are more preferably those comprising ω3 fatty acids. The ω3 fatty acids in the raw material may constitute any lipids including phospholipids, neutral fats, and other lipids, but at least part of the ω3 fatty acids preferably constitutes a phospholipid. That is, in the embodiment of the present disclosure, a method of producing a lipid composition is provided, wherein the lipid composition preferably comprises a phospholipid, and more preferably comprises an ω3 fatty acid comprised in a phospholipid. Preferably, no lower than 3% by mass, more preferably no lower than 5% by mass of the total lipid in the raw material is phospholipid. Preferably, no higher than 54% by mass, more preferably no higher than 39% by mass of the total lipid in the raw material is phospholipid. The proportion by mass of the phospholipids in the total lipids of the raw material may be determined by any of the methods known to those skilled in the art, such as thin-layer chromatography.

In the present disclosure, the terms "aquatic product resource" and "aquatic resource" are used interchangeably, and these terms encompass fish and non-fish aquatic organisms, including those collected in the sea as well as those collected in fresh water. The term "aquatic product processing" means processing these aquatic organisms for the purpose of food production or the like. Examples of the aquatic resources that comprise phospholipid-constituting 3 fatty acids as mentioned above and that may be used as a raw material for the method of one embodiment of the present disclosure include aquatic organisms such as mollusks including shellfish, such as Hotate. and squids, and arthropods such as krill, as well as various types of fish eggs such as ikura. The byproducts generated during the aquatic product processing, such as the midgut glands, gonads, mantles, and gills of Hotate-gai and the eyeballs, buccal bulbs, and skins of squids, may also be used suitably. The use of such byproducts is convenient because it can reduce the costs for disposing the byproducts and contribute to effective utilization of the marine resources. Moreover, in addition to the aquatic resources, soy beans, egg yolks, porcine livers, etc. can also provide raw materials of phospholipids. Further, it has become known in the recent years that the microalgae of the genus *Botryococcus* comprise unsaturated fatty acids such as linolenic acid as well as the phospholipids made up by them, and such materials may also be employed as the raw materials for the method according to the embodiment of the present disclosure.

Figure 2:
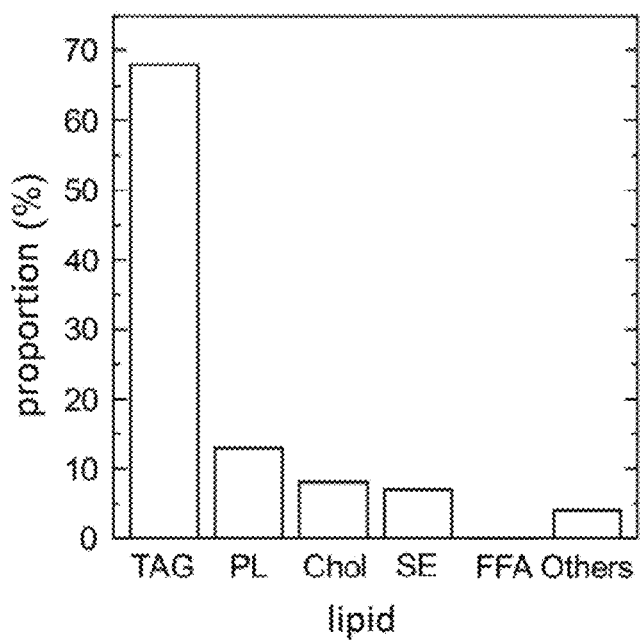
FIG. 2 shows the constituents of the lipids extracted with a chloroform-methanol mixed solvent (volume ratio=2:1) from the midgut glands generated during the processing of Hotate in Aomori Prefecture. TAG stands for triacylglycerols, PL for phospholipids, Chol for cholesterols, SE for sterol esters, and FFA for free fatty acids.
Figure 3:
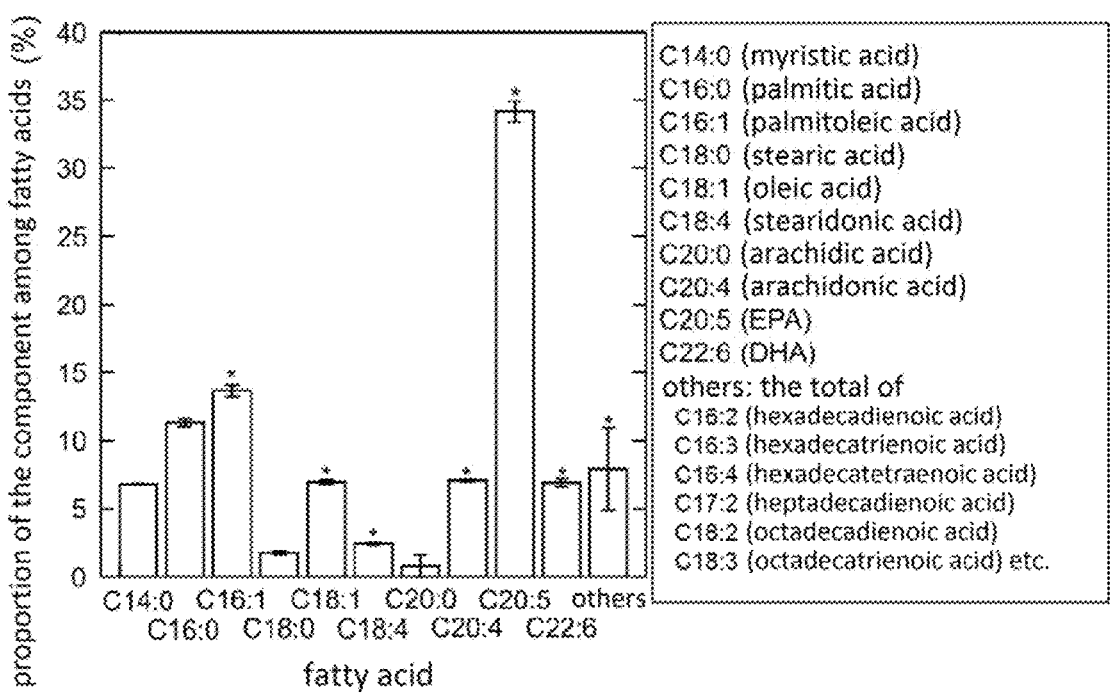
FIG. 3 shows the fatty acid constitutions comprised in the lipids that were extracted with a chloroform-methanol mixed solvent (volume ratio=2:1) from the midgut glands generated during the processing of Hotate in Aomori Prefecture. The error bars indicate the highest and the lowest values. The asterisks indicate unsaturated fatty acids.

From these raw materials, a suitable one is selected by considering the amount of the target ω3 fatty acids contained therein etc. For example, preferable raw materials which comprise EPA and DHA as ω3 fatty acid components and which are rich in phospholipids include the midgut glands, gonads, mantles, and gills of Hotate-gai and the eyeballs, buccal bulbs, and skins of squids, as well as krill, ikura, and the like. The byproducts generated during the aquatic product processing of Hotate-gai, Surume-ika and the like comprise EPA and DHA as the components of the phospholipids or the neutral fats, and they are extremely useful raw materials that are rich in the ω3 fatty acids. For instance, a lipid extracted from the midgut glands generated during the processing of Hotate in Aomori Prefecture comprised about 13% by mass of phospholipids and about 68% by mass of triacylglycerols (the rest of it comprised cholesterols, sterol esters, glycolipids, and the like), and 75 to 80% of the fatty acids constituting these lipids were unsaturated fatty acids, with EPA being the most abundant at about 34% (DHA was about 7%) (see FIGS. 2 and 3). Two or more types of raw materials such as those mentioned above may be used in combination as needed. In the following descriptions, the embodiments of the present disclosure will be described for the cases where EPA and DHA are the target ω3 fatty acids, but needless to say, other ω3 fatty acids, or ω6 fatty acids such as arachidonic acid, may also be targeted.

The raw materials such as those described above may be used directly in a hydrated state, without being dried. In general, hydrated raw materials with a water content of about 60 to 85% by mass may be suitably used, but the method of the present disclosure may also be used on the raw materials in which the water content has become lower than this due to freeze drying or the like (e.g. a raw material having a water content of 50% or higher). The water content can be calculated by drying the sample following the lipid extraction, for example by drying it with hot air at 105° C. or leaving it in a constant temperature chamber, measuring the dry weight when a constant weight is achieved, and subtracting this dry weight and the weight of the lipids from the total weight of the hydrated raw material. In the present specification, "water" in a "hydrated" state may comprise both the water originating from the biological tissues of the raw material and the water added externally (such as sea water and washing water).

It is preferable to perform a treatment to inactivate the enzymes by heating the raw material, prior to the extraction treatment, in order to prevent the progress of the biological reactions of the enzymes comprised in the raw material. The heat treatment is performed by submerging the hydrated raw material in water heated to, for example, 65° C. or higher, preferably 70° C. or higher, more preferably 80° C. or higher, and still more preferably 90° C. or higher. The duration of the heat treatment can be determined by a person skilled in the art as appropriate, but it is typically 10 minutes or shorter. The raw material after the heat treatment may be cooled in the air or in water, and then stored refrigerated or frozen.

It is further preferable to crush (or pulverize) the raw material prior to the extraction treatment, as this will improve the efficiency of the lipid extraction due to the increase in the area of contact with the extraction solvent. The crushing in the hydrated state is referred to as wet crushing. As to the method of crushing, physical crushing using the cutting blades may be used generally suitably, but any known methods may be chosen as appropriate. It is preferable to prepare the hydrated raw material into a paste-like state by the crushing (or pulverization). Other physical crushing methods include ultrasonic method, freeze-and-thaw method, osmotic shock method, grinding method using the beads, solid powder, or the like, homogenizer method, and French-press method using the searing force caused by forced extrusion from the pores.

By adding the polar solvent and the nonpolar solvent to the raw material as described above and mixing them (extraction treatment), the lipids will leach into the mixed organic solvent. For the extraction treatment, the mixed solvent comprising the polar solvent and the nonpolar solvent may be prepared beforehand and then added to the raw material, or, the polar solvent and the nonpolar solvent may be added individually to the raw material to prepare the mixed solvent as a result of such additions. In the latter case, either the polar solvent or the nonpolar solvent may be added first to the raw material. If the raw material that has undergone the wet crushing is combined with the polar solvent, shaken and mixed, and then combined with the nonpolar solvent, the water comprised in the raw material will first mix with the polar solvent, facilitating the contact between the solvent and the raw material.

The extraction treatment may be suitably carried out at an ambient temperature, for example at an extraction temperature of about 10 to 40° C. The extraction mode may be either a batch mode or a continuous mode. Preferably, the raw material and the extraction solvent are mixed well by stirring or shaking to provide a good contact between them, and a sufficient extraction time is provided. Preferably, the stirring or the shaking is continued for about 30 minutes to sufficiently mix the raw material and the extraction solvent. In the batch mode, the solvent extraction may be repeated two or more times, and the extract obtained in each round of extraction may be combined with the others, to increase the recovery yields of the lipids. Counter current extraction is preferable in terms of work efficiency and economy, and a semi-counter current multi-stage extraction device, a mixer-settler type extraction device, a tower-type extraction device, a counter current-type centrifugal extraction device, or the like may be used to suitably carry out the continuous counter current extraction.

The polar solvent comprised in the extraction solvent may be, for example, a lower alcohol (an alcohol with a carbon number of 1 to 5) such as methanol, ethanol, 1-propanol, 2-propanol, and 1-butanol, acetone, acetonitrile, THF (tetrahydrofuran), DMF (N,N-dimethylformamide) or the like, and two or more types may be used in combination. Preferably, ethanol or methanol, more preferably ethanol is used. The nonpolar solvent may be, for example, a linear, branched, or cyclic alkane with a carbon number of 5 to 8, such as n-hexane, diethyl ether, t-butyl methyl ether, ethyl acetate, chloroform, methylene chloride, benzene, toluene, or the like, and two or more types may be used in combination. Preferably, n-pentane, n-hexane, n-heptane, or t-butyl methyl ether, more preferably n-hexane is used. It is especially preferable if the polar solvent is a lower alcohol and the nonpolar solvent is a linear alkane with a carbon number of 5 to 8, and it is most preferable if the polar solvent is ethanol and the nonpolar solvent is n-hexane.

The amount of the polar solvent used may be adjusted to about 1 to 5 parts by weight, preferably about 2 to 4 parts by weight, relative to 1 part by weight (wet weight) of the hydrated raw material, and the amount of the nonpolar solvent used may be adjusted to about 1 to 10 parts by weight, preferably about 1 to 5 parts by weight, relative to 1 part by weight of the hydrated raw material. To inhibit peroxidation of the lipids, about 0.01 to 0.2% by mass, relative to the mass of the hydrated raw material, of an antioxidant (e.g. γ-tocopherol, α-tocopherol, or a mixed tocopherol) may be added to the hydrated raw material beforehand.

Typically, about 60 to 85% by mass of the raw material for aquatic product processing is water. Once the solvent extraction is started, the lipids comprised in the raw material (accounting for about 3 to 21% by mass of the hydrated raw material) will move into the extraction solvent, and at the same time, the water comprised in the raw material will mix with the polar solvent, and the insolubles will be left as a solid fraction (about 15 to 31% by dry mass).

By removing the insoluble solid fraction from the mixture of the extract solution and the insoluble solid fraction that are obtained from the extraction treatment, an extract solution comprising the lipids is obtained. The removal of the solids can be carried out by selecting a suitable method from common solid-liquid separation methodologies, such as sedimentation, filtration, and centrifugation. The removal of the solids may be carried out during the separation treatment of the extract solution described below. As needed, in order to improve the recovery yields of the lipids by extraction, a polar solvent and a nonpolar solvent as described above may be added again to the collected solid fraction to repeat the extraction treatment. In general, about 80% by mass of the total lipids comprised in the raw material may be extracted by a single round of extraction, and about 98% by mass or more of the total lipids may be extracted by two rounds of extraction.

The extract solution obtained from the extraction treatment is a mixture of the polar solvent and the nonpolar solvent, which will be subjected to a separation treatment to separate it into a polar solvent phase and a nonpolar solvent phase. For the separation treatment, centrifugation or the like is applied to facilitate the separation based on the different specific gravities. If the extraction treatment is conducted more than once, the extract solutions obtained after the removal of the solids in different rounds of extraction may be combined to perform the separation treatment thereon, or, the separation treatment may be performed on the extract solution obtained in each round of extraction. If the removal of the solid fraction described above is to be performed concurrently with the separation treatment, the extract solution still containing the insoluble solids is subjected to the separation treatment, and the separated polar and nonpolar solvent phases are then each taken away. Following this, the solvents may be added to the solid fraction to repeat the extraction treatment and the separation treatment, whereafter the separated polar and nonpolar solvent fractions, respectively, are combined among themselves and each of the combined fractions is subjected to the subsequent treatments. The centrifugal force used in the centrifugation is a force that is sufficient to separate the polar solvent phase and the nonpolar solvent phase, which is preferably about 1,000 to 3,000×g, or about 1,500 to 2,500×g, for example about 2.000×g. The length of time for the centrifugation is a length that is sufficient to separate the polar solvent phase and the nonpolar solvent phase, and for example, the centrifugation is carried out for about 5 to 10 minutes, preferably for several minutes. The temperature for the centrifugation is for example near room temperature, and specifically, the temperature may be about 10 to 30° C. These parameters may be determined as needed depending on the volume of the extract solution etc.

Due to phase separation, the lipids comprised in the extract solution are separated into a first lipid fraction comprised in a polar solvent phase and a second lipid fraction comprised in a nonpolar solvent phase. In general, after a separation treatment of the extract solution obtained from two rounds of extraction, the polar solvent phase comprises a first lipid fraction equivalent to about 1 to 10% by mass of the total lipids that were comprised in the raw material, and the nonpolar solvent phase comprises a second lipid fraction equivalent to 90% by mass or more of the total lipids. The proportion of the phospholipids in the first lipid fraction is generally 70% by mass or higher. In the second lipid fraction, the proportion of the triacylglycerols is generally about 35 to 75% by mass, and the proportion of the phospholipids is generally about 10 to 30% by mass.

The polar solvent and the nonpolar solvent comprised in the polar solvent phase and the nonpolar solvent phase separated by the separation treatment can be each recovered. The solvents can be recovered by any methods known to those skilled in the art, but solvent recovery by distillation is suitable. The recovered solvents can be re-used, and especially, re-used in the extraction treatment as described above.

The polar solvents which mix with water, especially ethanol, show poorer recovery rates compared to the nonpolar solvents such as n-hexane, due to the co-boiling with water. However, in the extraction treatment according to the present disclosure, the polar solvent is combined with the nonpolar solvent and used as merely a part of the mixed organic solvent. Therefore, use of the polar solvent can be reduced compared to other methods where the extraction solvent solely comprises the polar solvent.

The solvent recovery step may comprise recovering the polar solvent from the polar solvent phase, recovering the nonpolar solvent from the nonpolar solvent phase, or both. As described below, if the nonpolar solvent phase is contacted with an adsorbent to perform a purification treatment of the second lipid fraction, it will be preferable to recover the nonpolar solvent after the purification treatment.

The removal of the solvents can be performed according to conventional methods, by using known drying techniques such as evaporation under a reduced pressure, spray drying, and freeze drying as appropriate. Heating and a contact with oxygen gas may be preferably avoided, as they would otherwise facilitate oxidation or degeneration of the lipids. Thus, the solvents are preferably evaporated in a non-oxidizing atmosphere at a temperature of about 80° C.

The first lipid fraction of the polar solvent phase may include water-soluble or hydrophilic substances as impurities, specific examples of which may include arsenobetaine and proteinous water-soluble organic substances. On the other hand, the second lipid fraction of the nonpolar solvent phase may include lipophilic impurities, specific examples of which may include porphyrin complexes of magnesium and copper and their analogues. A purification treatment may be conducted to remove the impurities from the second lipid fraction of the nonpolar solvent phase. Undesirable coloring or odor of the product can be thereby removed, to provide a lipid product of higher quality.

The impurities dissolved in the nonpolar solvent phase, such as the porphyrin complexes of magnesium and copper, can be removed by performing contact-stirring following the addition of an adsorbent such as activated carbon, activated clay, and silica gel. The amount of the adsorbent added is preferably about 1 to 10% of the weight of the lipids dissolved in the nonpolar solvent phase. Deodorization of the lipids may be achieved by using molecular distillation, steam distillation or the like, as well. For the purification, addition of an adsorbent to the nonpolar solvent phase followed by contact-stirring, or molecular distillation or steam distillation on the lipids after the evaporation of the nonpolar solvent phase may be performed, and any one or more of these treatments may be performed. However, if steam distillation is to be conducted, the phospholipid which is a component of the lipids needs to be removed by degumming before the steam distillation.

In order to obtain a lipid composition of a desired constitution, it is preferable to measure the amounts of phospholipids, neutral fats, and the target ω3 fatty acid components (as acyl residues) comprised in the lipids, by performing a composition analysis of the lipid fractions, e.g. the second lipid fraction. Based on these measurements, the lipid fractions obtained from separate extraction processes can be combined. For example, a predetermined goal may be set for each of the target ω3 fatty acid content and the triacylglycerol and phospholipid contents, and the second lipid fractions obtained from separate extraction processes may be combined in a certain blending ratio such that this predetermined goal is met, to prepare a lipid composition of consistent quality. The composition analysis of the lipid fractions obtained may be performed by any analytical methods commonly used for lipids. For example, the lipid compositions can be analyzed by using thin layer chromatography/hydrogen flame ionization detector (TLC/FID), and the fatty acid compositions can be analyzed by using gas chromatography. For the fatty acid components comprised in the lipids, the free fatty acids obtained through saponification of the lipids and ether extraction of the unsaponifiables may be methyl-esterified to enable the analysis by gas chromatography. The amount of each component is determined based on the peak areas detected and a pre-obtained calibration curve. The lipid composition analysis may be performed by using forward phase TLC, forward phase HPLC, or the like.

Figure 4:
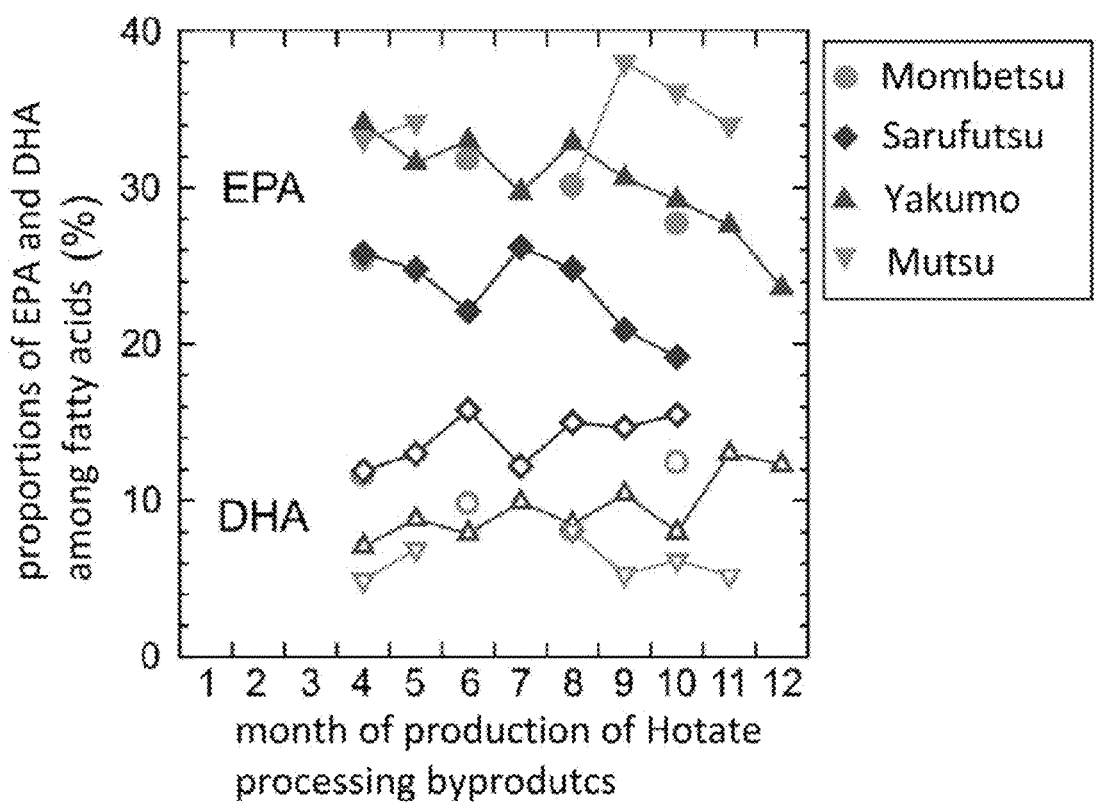
FIG. 4 shows the monthly changes of the concentrations of EPA and DHA as the components of the lipids extracted from the midgut glands generated during the processing of Hotate in Aomori Prefecture (Mutsu), and the monthly changes of the concentrations of EPA and DHA as the components of the lipids extracted from the midgut glands, gonads, mantles, and gills generated during the processing of Hotate in: Mombetsu City, Hokkaido; Sarufutsu Village, Soya District, Hokkaido; and Yakumo Town, Futami District, Hokkaido.
Figure 5:
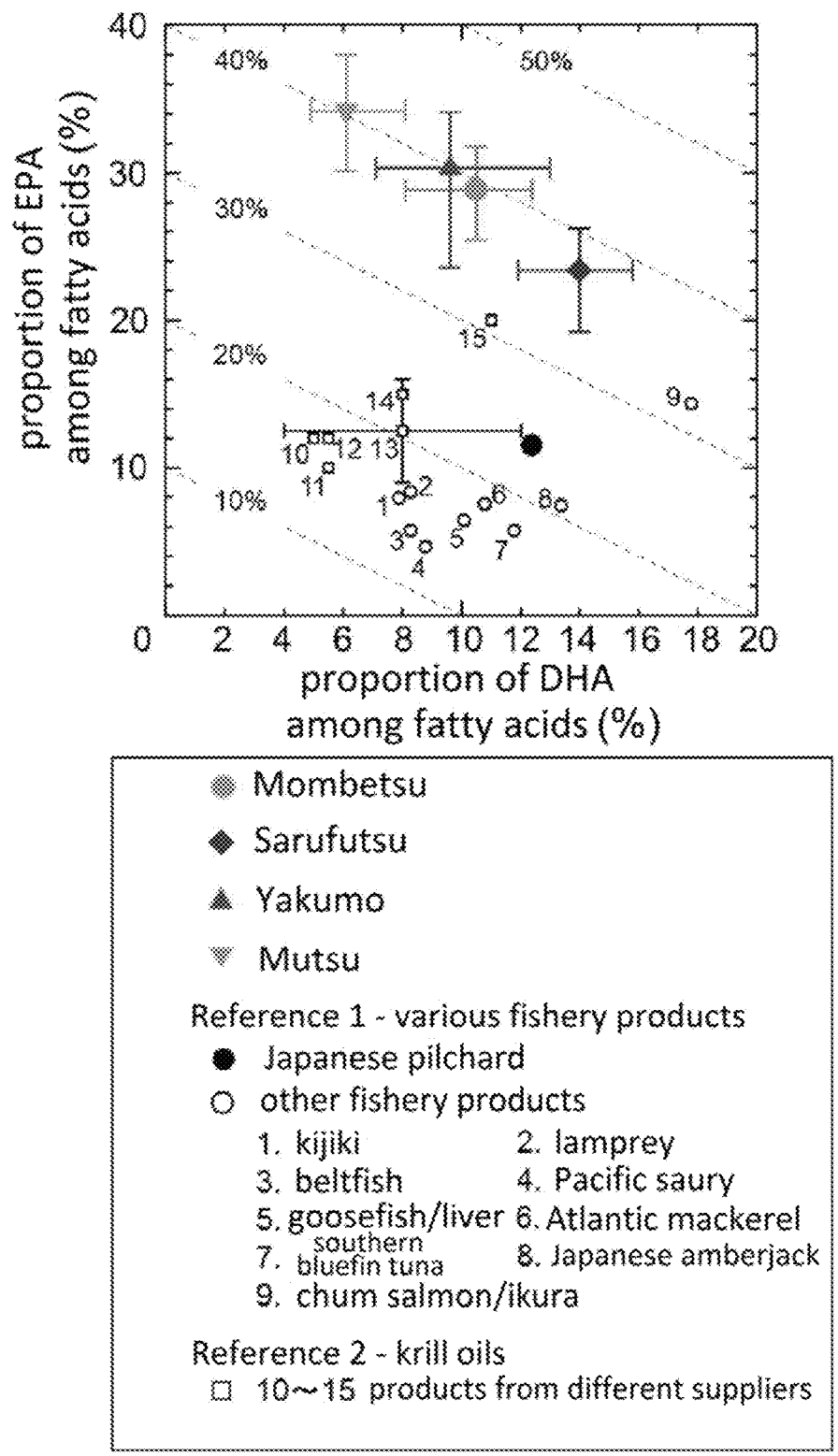
FIG. 5 shows the averages of the EPA concentrations and the averages of the DHA concentrations shown in FIG. 4. The places of origin in which the Hotate processing byproducts were generated are indicated in the lower panel. For comparison, the concentrations of EPA and DHA as the components of the lipids of various fishery products are shown. The concentrations of EPA and DHA as the components of krill oils are also shown. The EPA and DHA concentrations of the various fishery products are based on the food database of the Ministry of Education, Culture, Sports, Science and Technology. The EPA and DHA concentrations of the krill oils are based on the product specifications of the distributors. The error bars indicate the highest and the lowest values. The dotted lines indicate the sums of the EPA and DHA concentrations.

When a lipid composition is manufactured from a raw material that is a byproduct generated during the processing of Hotate-gai or Surume-ika, the lipid constituents and the fatty acid constitutions will vary depending on the places of origin of the byproduct as well as the seasons. Moreover, the lipid constituents as well as the ratio among the fatty acids could also become variable depending on which body parts the byproduct comprises and in what amounts the byproduct comprises them. For example, the proportion of the phospholipids comprised in the lipids of the Hotate-gai midgut glands generated during the processing of Hotate in Aomori Prefecture has varied in a range of about 3 to 16% by mass, and the combined EPA and DHA content has varied in a range of about 38 to 43% by mass. In Mombetsu City, Hokkaido; Sarufutsu Village, Soya District, Hokkaido; and Yakumo Town, Futami District, Hokkaido, where the byproducts generated during the processing of Hotate have comprised other body parts, i.e. gonads, mantles, and gills, in addition to the midgut glands, the proportion of the phospholipids has varied in a range of about 7 to 54% by mass, and the combined EPA and DHA content has varied in a range of about 34 to 43% by mass (FIGS. 4 and 5).

Therefore, the target ω3 fatty acid content will be set by considering the seasonal variations in the ω3 fatty acid content and in the phospholipid content, the place of origin of the raw material, and the monthly changes of the availability of the raw material. By appropriately adjusting the blending ratios depending on the seasonal changes in the constitutions of the raw materials and in the availability of the raw materials, it is possible to provide a lipid product rich in ω3 fatty acids wherein the variability in the lipid constitution is suppressed.

FIG. 1 shows an overview of the production of a lipid composition according to one embodiment of the present disclosure. In this embodiment, a lipid composition is produced and formulated by using only the nonpolar solvent phase (second lipid fraction). Ethanol, the polar solvent, and n-hexane, the nonpolar solvent, are each recovered by distillation (solvent recovery step), and re-used as extraction solvents. Polar and nonpolar solvents other than ethanol and n-hexane may also be used. The waste water treatment step and the formulation step are each optional. The heat treatment step, the wet crushing treatment step, the adsorption (purification treatment) step, and the solvent recovery step are each omissible, although it is preferable that these steps be not omitted. In this figure, the raw material is the byproducts generated during the processing of Hotate-gai, but this method can be applied to any types of raw materials containing lipids.

In the aquatic product resources as well as the byproducts produced during the processing thereof, heavy metals such as cadmium, lead, mercury, chromium, copper, and zinc, magnesium (or magnesium-containing compounds), arsenic (or arsenic-containing compounds), and the compounds such as dioxins (polychlorinated dibenzo-para-dioxins, polychlorinated dibenzofurans, and dioxin-like polychlorinated biphenyls) are accumulated. It has been discovered that the levels of cadmium, lead, mercury, chromium, copper, zinc, magnesium, and arsenic are extremely low in the nonpolar solvent phase obtained after the separation treatment step according to the present disclosure. That is, in the nonpolar solvent phase which has just undergone the separation treatment, the low levels shown below for example can be already achieved: cadmium concentration: 0.6 mg or lower per kg of lipid; lead concentration: 0.1 mg or lower per kg of lipid; mercury concentration: 0.02 mg or lower per kg of lipid; chromium concentration: 0.07 mg or lower per kg of lipid; copper concentration: 1.6 mg or lower per kg of lipid; zinc concentration: 4.2 mg or lower per kg of lipid; magnesium concentration: 400 mg or lower per kg of lipid; arsenic concentration: 8 mg or lower per kg of lipid; and dioxins concentration: 3.3 pg-TEQ per gram of lipid.

By a purification treatment which comprises contacting this nonpolar solvent phase containing the second lipid fraction with an adsorbent to remove the impurities from the nonpolar solvent phase, even lower cadmium, lead, mercury, chromium, copper, zinc, magnesium, arsenic, and dioxins concentrations than the above may be achieved. Specifically, after a purification treatment involving contacting the nonpolar solvent phase with an adsorbent and stirring for about 30 minutes, the cadmium concentration in the second lipid fraction may be 0.4 mg or lower per kg of lipid, more preferably 0.3 mg or lower per kg of lipid, and still more preferably 0.2 mg or lower per kg of lipid. After the purification treatment, the arsenic concentration in the second lipid fraction may be 3 mg or lower per kg of lipid, more preferably 2 mg or lower per kg of lipid, and still more preferably 1 mg or lower per kg of lipid.

As the adsorbent used in this purification treatment, an activated carbon is preferable, especially a food-purpose activated carbon.

In the conventional extraction methods, it was not just the concentrations of these toxic components that were not reduced in the extract solutions. That is, in the conventional extraction methods, other impurities besides cadmium and arsenic, for example magnesium and iron, were also included in the extract solutions at high amounts. Therefore, even if an adsorbent was employed, the impurities would compete with each other on the adsorbent thus interfering with the removal of the cadmium and arsenic. In the second lipid fractions obtained after the separation treatment according to the present disclosure, the lead, mercury, chromium, and dioxins contents were also reduced to extremely low, safe levels, whether or not an adsorbent was used (lead concentration of lower than 0.1 mg per kg of lipid, mercury concentration of lower than 0.01 mg per kg of lipid, chromium concentration of lower than 0.05 mg per kg of lipid, and dioxins concentration of lower than 0.03 pg-TEQ per gram of lipid).

By using a raw material richly comprising phospholipids and having a high EPA content, such as the byproducts generated during the processing of Hotate-gai, and by performing an extraction treatment, a separation treatment, and optionally a purification treatment on the nonpolar solvent phase with an adsorbent, to obtain a second lipid fraction from the nonpolar solvent phase according to the present disclosure, a lipid composition can be obtained wherein the EPA to DHA mass ratio (EPA/DHA) in the fatty acids comprised in the lipid is 1.2 to 7.2, the proportion of phospholipid in the total lipid is no lower than 3% by mass and no higher than 54% by mass, the cadmium concentration is 0.4 mg or lower per kg of lipid, the arsenic concentration is 3 mg or lower per kg of lipid, and the dioxins concentration is 2 pg-TEQ or lower per gram of lipid. The EPA to DHA mass ratio (EPA/DHA) in the fatty acids comprised in the lipid of the lipid composition is preferably no lower than 1.9, more preferably no lower than 3.4. The proportion of phospholipid in the total lipid of the lipid composition is preferably no lower than 3% by mass, more preferably no lower than 10% by mass, and still more preferably no lower than 18% by mass. The proportion of phospholipids in the total lipid of the lipid composition is preferably no higher than 54% by mass, more preferably no higher than 45% by mass, and still more preferably no higher than 39% by mass.

The apparatus for producing a lipid composition or the system for producing a lipid composition according to the present disclosure is an apparatus or a system with which the production of the lipid composition described above can be carried out. That is, this apparatus or system comprises: an extraction treatment component for extracting a lipid comprised in a hydrated raw material by using a mixed extraction solvent comprising a polar solvent and a nonpolar solvent; and a separation treatment component for separating an extract obtained in the extraction treatment component into a polar solvent phase comprising a first lipid fraction, a nonpolar solvent phase comprising a second lipid fraction, and a solid fraction phase.

This apparatus or system may further comprise a purification treatment component for contacting the nonpolar solvent phase separated in the separation treatment component with an adsorbent to remove a remaining impurity from the nonpolar solvent phase. Also, this apparatus or system may further comprise a solvent recovery component for recovering the polar solvent and the nonpolar solvent from the polar solvent phase and the nonpolar solvent phase separated in the separation treatment component, respectively. Also, this apparatus or system may further comprise a heat treatment component for heating the hydrated raw material at a temperature of 65° C. or higher. Also, this apparatus or system may further comprise a wet crushing component for crushing the hydrated raw material.

EXAMPLES

<Content Analysis of the Byproducts Generated During the Processing of Hotate>

The midgut glands, gonads, mantles, and gills of Hotate-gai generated during the processing of Hotate in Yakumo Town, Futami District, Hokkaido, were obtained, and using Sample 1 in which they were treated with boiling water, the following measurements were made.

(Quantitation of Total Lipids and Solids)

The Hotate-gai midgut glands, gonads, mantles, and gills adjusted to the combined amount of 100 g were finely crushed, and subjected to a solvent extraction by adding 700 mL of chloroform-methanol mixed solvent (volume ratio=2:1). By removing the solids from the extract solution and then evaporating the solvents, an oily material was obtained as total lipids. The mass of this oily material was measured and determined to be 7.6 g (7.6% by mass of the hydrated raw material). The post-extraction residue was dried in a constant temperature chamber set at the temperature of 105° C. until a constant weight was achieved, and 21.8 g of solids were recovered.

The midgut glands, gonads, mantles, and gills generated during the processing of Hotate in Mombetsu City, Hokkaido, were obtained, and using Sample 2 in which they were treated with boiling water, the same content analysis as described above was carried out. The total lipid content was 5.6% by mass of the hydrated mass. Further, the midgut glands, gonads, mantles, and gills generated during the processing of Hotate in Sarufutsu Village, Soya District, Hokkaido, were obtained, and using Sample 3 in which they were treated with boiling water, the same content analysis as described above was also carried out. The total lipid content was 6.6% by mass of the hydrated mass. Similarly, the midgut glands of Hotate-gai generated during the processing of Hotate in Aomori Prefecture were obtained, and using Sample 4 in which they were treated with boiling water, the same content analysis as described above was also carried out. The total lipid content was 12.9% by mass of the hydrated mass.

<Sample 1>

(Extraction Treatment and Separation Treatment)

Two hundred and nineteen grams of Hotate-gai midgut glands, gonads, mantles, and gills were crushed into a paste by using a food processor, and this was combined with 100 mL of 95% ethanol and 250 mL of n-hexane and shaken for 30 minutes (first extraction). This was centrifuged for 10 minutes at 3000 rpm (900×g) to separate the extract solution into an n-hexane phase, an ethanol-water phase, and a solid fraction, and each of the n-hexane phase and the ethanol-water phase was individually placed in a container (first separation treatment). The remaining solid residue was again combined with 100 mL of 95% ethanol and 250 mL of n-hexane, and a second extraction treatment and a second separation treatment were carried out under the same conditions described above. The two ethanol-water phases were combined, and the amount of the first lipid fraction comprised therein was investigated and determined to be 0.75 g. The two n-hexane phases were combined, and the amount of the second lipid fraction comprised therein was investigated and determined to be 16.15 g. Therefore, the first lipid fraction was about 4.4% of the total lipid, while the second lipid fraction was about 94.4% of the total lipid, and the lipid recovery yield in the extraction treatment was 98.8%.

(Composition Analysis)

For each of the first lipid fraction and the second lipid fraction, the phospholipid and neutral fat contents were measured by using thin-layer chromatography. The results showed a phospholipid content of 56% by mass and a triacylglycerol content of no higher than 1% by mass in the first lipid fraction, and a phospholipid content of 9% by mass and a triacylglycerol content of 43% by mass in the second lipid fraction. Further, the proportions of EPA and DHA among the fatty acids comprised in the lipids were investigated by gas chromatography, wherein the proportion of EPA was 26% by mass and the proportion of DHA was 11% by mass in the first lipid fraction. The proportion of EPA was 32% by mass and the proportion of DHA was 9% by mass in the second lipid fraction <Sample 2>

Using 50.3 g of Hotate-gai midgut glands, gonads, mantles, and gills, the crushing, the extraction treatment, and the separation treatment were carried out similarly to Sample 1 to obtain an ethanol-water phase and an n-hexane phase. The amounts of the first and the second lipid fractions comprised in the respective phases were investigated, wherein the first lipid fraction was 0.75 g and the second lipid fraction was 0.96 g. Therefore, the first lipid fraction was about 27% of the total lipids and the second lipid fraction was about 34% of the total lipids, and the recovery yield in the extraction was 61%. Further, for each of the first lipid fraction and the second lipid fraction, the phospholipid and triacylglycerol contents as well as the proportions of EPA and DHA were investigated by the same methods as described for Sample 1. In the first lipid fraction, the phospholipid content was 47% by mass, the triacylglycerol content was no higher than 1% by mass, the proportion of EPA was 16% by mass, and the proportion of DHA was 25% by mass. In the second lipid fraction, the phospholipid content was 31% by mass, the triacylglycerol content was 33% by mass, the proportion of EPA was 24% by mass, and the proportion of DHA was 15% by mass.

<Sample 3>

Using 50.1 g of Hotate-gai midgut glands, gonads, mantles, and gills, the crushing, the extraction treatment, and the separation treatment were carried out similarly to Sample 1 to obtain an ethanol-water phase and an n-hexane phase. The amounts of the first and the second lipid fractions comprised in the respective phases were investigated, wherein the first lipid fraction was 0.07 g and the second lipid fraction was 3.2 g. Therefore, the first lipid fraction was about 2% of the total lipids and the second lipid fraction was about 97% of the total lipids, and the recovery yield in the extraction was 99%/o. Further, for each of the first lipid fraction and the second lipid fraction, the phospholipid and triacylglycerol contents as well as the proportions of EPA and DHA were investigated by the same methods as described for Sample 1. In the first lipid fraction, the phospholipid content was 47% by mass, the triacylglycerol content was no higher than 1% by mass, the proportion of EPA was 23% by mass, and the proportion of DHA was 16% by mass. In the second lipid fraction, the phospholipid content was 29% by mass, the triacylglycerol content was 49% by mass, the proportion of EPA was 36% by mass, and the proportion of DHA was 8% by mass.

<Sample 4>

Using 50.3 g of Hotate-gai midgut glands, the crushing, the extraction treatment, and the separation treatment were carried out similarly to Sample 1 to obtain an ethanol-water phase and an n-hexane phase. The amounts of the first and the second lipid fractions comprised in the respective phases were investigated, wherein the first lipid fraction was 0.3 g and the second lipid fraction was 6.1 g. Therefore, the first lipid fraction was about 5% of the total lipids and the second lipid fraction was about 95% of the total lipids, and the recovery yield in the extraction was about 100%. Further, for each of the first lipid fraction and the second lipid fraction, the phospholipid and triacylglycerol contents as well as the proportions of EPA and DHA were investigated by the same methods as described for Sample 1. In the first lipid fraction, the phospholipid content was 58% by mass, the triacylglycerol content was no higher than 1% by mass, the proportion of EPA was 30% by mass, and the proportion of DHA was 6% by mass. In the second lipid fraction, the phospholipid content was 20% by mass, the triacylglycerol content was 50% by mass, the proportion of EPA was 35% by mass, and the proportion of DHA was 7% by mass.

<Analysis of Impurities in the Nonpolar Solvent Phase (Second Lipid Fraction)>

Figure 6:
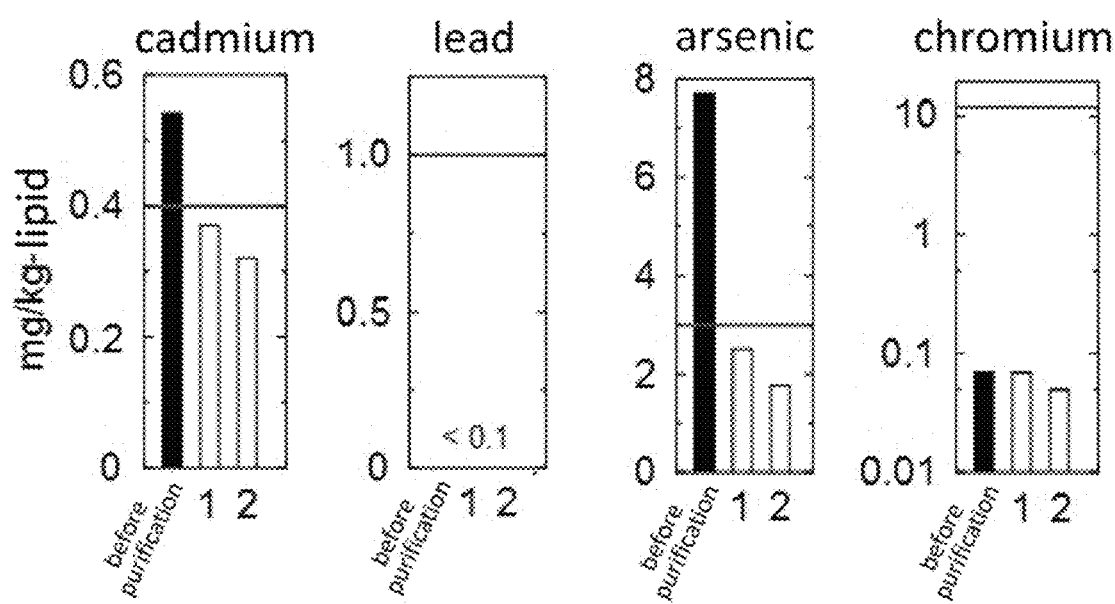
FIG. 6 shows the impurity concentrations in the second lipid fraction before and after the purification treatment. "1" and "2" on the horizontal axis represent different food-purpose activated carbon products.

Using the byproducts generated during the processing of Hotate-gai as a raw material, a heat treatment, a wet crushing treatment, an extraction treatment, and a separation treatment were carried out according to the present disclosure, and thereafter, the concentrations of cadmium, lead, arsenic, and chromium in the n-hexane (nonpolar solvent) phase were measured. Elemental analysis was carried out by using ICP-AES after removal of the solvents. Further, following a purification treatment in which the n-hexane phase was combined with 5% by weight, relative to the weight of the lipid dissolved therein, of a powder-form activated carbon adsorbent and contact-stirred for 30 minutes, the concentrations of these impurities were measured again. The results are shown in FIG. 6. The concentrations of these impurities are shown in mg amount per kg of lipid. The horizontal lines in the graphs show the standards for reference. The standard for cadmium concentration is based on the international standard for polished rice (0.4 mg/kg) from FAO/WHO Codex Alimentarius (Notably, the international standard for marine clams is less strict, being 2 mg/kg). The standard for lead concentration is based on Food Chemical Codex, and the standard for arsenic concentration is based on Food Chemical Codex and European Union E322. It is noted that chromium as well as iron, copper, and zinc is an element that is essential for the maintenance of health, but it is recommended in France to keep the chromium consumption at no higher than 30 μg per day. Thus, based on the daily consumption of EPA and DHA (1 g) and the EPA and DHA concentrations in the second lipid fraction found above (about 40%), the upper limit of chromium concentration (12 mg/kg) was calculated. From this figure, it can be understood that the concentrations of the toxic impurities are limited to extremely low levels in the second lipid fraction and its safety is sufficiently ensured as it is, but it could satisfy even stricter standards with the purification treatment.

In the embodiments of the present disclosure: the raw materials such as aquatic resources can be used while remaining in a hydrated state and not dried; the extraction as well as separation/collection/purification of the lipids from the raw materials comprising phospholipids can be carried out efficiently and conveniently; and a lipid product which richly comprises phospholipids and ω3 fatty acids, especially EPA, and in which the impurity levels are within the international standards, can be manufactured. Therefore, it is possible to provide the product as a dietary supplement, a food additive, a pharmaceutical ingredient, or the like. In the embodiments of the present disclosure, provision of lipid products whose constitutions fall within a constant range can be easily managed despite the compositional variability of the raw materials due to the regional and seasonal differences. The embodiments of the present disclosure could contribute to a reduction of the costs associated with the disposal of the byproducts generated during the processing of the aquatic resources, as well as to effective utilization of the unused resources, thereby contributing to facilitation of recycling and environmental protection.

What is claimed is:

1. A method of producing a lipid composition, the method comprising:
    an extraction treatment step to extract a lipid comprised in a hydrated raw material by using an extraction solvent comprising a polar solvent and a nonpolar solvent;
    a separation treatment step to separate an extract solution obtained in the extraction treatment step into a polar solvent phase comprising a first lipid fraction and a nonpolar solvent phase comprising a second lipid fraction; and
    a purification treatment step to remove an impurity from the nonpolar solvent phase by contacting the nonpolar solvent phase obtained in the separation treatment step with an adsorbent;
    wherein the hydrated raw material comprises at least one byproduct of aquatic product processing selected from midgut gland, gonad, mantle, and gill of a Hotate-gai and eyeball, buccal bulb, and skin of a squid.

2. The method of producing a lipid composition according to claim 1, further comprising a solvent recovery step to recover the polar solvent and the nonpolar solvent from the polar solvent phase and the nonpolar solvent phase obtained in the separation treatment step, respectively.

3. The method of producing a lipid composition according to claim 1, wherein the polar solvent comprises a lower alcohol, acetone, acetonitrile, THF, DMF, or a combination thereof.

4. The method of producing a lipid composition according to claim 1, wherein the nonpolar solvent comprises an alkane with a carbon number of 5 to 8, diethyl ether, t-butyl methyl ether, ethyl acetate, chloroform, methylene chloride, benzene, toluene, or a combination thereof.

5. The method of producing a lipid composition according to claim 1, wherein no lower than 3% by mass of the total lipid comprised in the hydrated raw material is phospholipid.

6. The method of producing a lipid composition according to claim 1 wherein, for the extraction treatment step, the extraction solvent is prepared beforehand as a mixed organic solvent using the polar solvent and the nonpolar solvent and then added to the hydrated raw material, or, the polar solvent and the nonpolar solvent are added individually and sequentially to the hydrated raw material to prepare the mixed organic solvent by virtue of the additions.

7. The method of producing a lipid composition according to claim 1, wherein the hydrated raw material comprises water at a water content of 60 to 85% by weight.

8. The method of producing a lipid composition according to claim 1 wherein, in the extraction treatment step, the polar solvent and the nonpolar solvent are used at 1 to 5 parts by weight and 1 to 10 parts by weight, respectively, relative to 1 part by wet weight of the hydrated raw material.

9. The method of producing a lipid composition according to claim 1, further comprising a heat treatment step to heat the hydrated raw material at a temperature of 65° C. or higher.

10. A method of producing a lipid composition, the method comprising:
a wet crushing step to crush a hydrated raw material;
an extraction treatment step to extract a lipid comprised in the hydrated raw material by using an extraction solvent comprising a polar solvent and a nonpolar solvent; and
a separation treatment step to separate an extract solution obtained in the extraction treatment step into a polar solvent phase comprising a first lipid fraction and a nonpolar solvent phase comprising a second lipid fraction;
wherein the hydrated raw material comprises at least one byproduct of aquatic product processing selected from midgut gland, gonad, mantle, and gill of a Hotate-gai and eyeball, buccal bulb, and skin of a squid.

11. The method of producing a lipid composition according to claim 10, further comprising a solvent recovery step to recover the polar solvent and the nonpolar solvent from the polar solvent phase and the nonpolar solvent phase obtained in the separation treatment step, respectively.

12. The method of producing a lipid composition according to claim 10, wherein the polar solvent comprises a lower alcohol, acetone, acetonitrile, THF, DMF, or a combination thereof.

13. The method of producing a lipid composition according to claim 10, wherein the nonpolar solvent comprises an alkane with a carbon number of 5 to 8, diethyl ether, t-butyl methyl ether, ethyl acetate, chloroform, methylene chloride, benzene, toluene, or a combination thereof.

14. The method of producing a lipid composition according to claim 10, wherein no lower than 3% by mass of the total lipid comprised in the hydrated raw material is phospholipid.

15. The method of producing a lipid composition according to claim 10 wherein, for the extraction treatment step, the extraction solvent is prepared beforehand as a mixed organic solvent using the polar solvent and the nonpolar solvent and then added to the hydrated raw material, or, the polar solvent and the nonpolar solvent are added individually and sequentially to the hydrated raw material to prepare the mixed organic solvent by virtue of the additions.

16. The method of producing a lipid composition according to claim 10, wherein the hydrated raw material comprises water at a water content of 60 to 85% by weight.

17. The method of producing a lipid composition according to claim 10 wherein, in the extraction treatment step, the polar solvent and the nonpolar solvent are used at 1 to 5 parts by weight and 1 to 10 parts by weight, respectively, relative to 1 part by wet weight of the hydrated raw material.

18. The method of producing a lipid composition according to claim 10, further comprising a heat treatment step to heat the hydrated raw material at a temperature of 65° C. or higher.

19. A method of producing a lipid composition, the method comprising:
a wet crushing step to crush a hydrated raw material into a paste;
and following the wet crushing step, an extraction treatment step to extract a lipid comprised in the hydrated raw material by using an extraction solvent comprising a polar solvent and a nonpolar solvent in combination, wherein the polar solvent is a lower alcohol and the nonpolar solvent is an alkane with a carbon number of 5 to 8; and
a separation treatment step to separate by centrifugation an extract solution obtained in the extraction treatment step into a polar solvent phase comprising a first lipid fraction, a nonpolar solvent phase comprising a second lipid fraction, and a solid fraction phase;
wherein the hydrated raw material comprises water at a water content of 60 to 85% by weight, and
wherein the hydrated raw material comprises at least one byproduct of aquatic product processing selected from midgut gland, gonad, mantle, and gill of a Hotate-gai.

20. The method of producing a lipid composition according to claim 19, wherein the polar solvent is ethanol and the nonpolar solvent is n-hexane.

* * * * *